United States Patent [19]

Schwarz et al.

[11] 4,344,961
[45] Aug. 17, 1982

[54] INSECTICIDAL BENZYLFURYLMETHYL ESTERS OF 3-(2,2-DICHLOROVINYL)-2,2-DIMETHYL-CYCLOPROPANE CARBOXYLIC ACIDS

[75] Inventors: Gerd-Ulrich Schwarz, Mannheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 232,557

[22] Filed: Feb. 9, 1981

Related U.S. Application Data

[63] Continuation of Ser. No. 96,520, Nov. 21, 1979, abandoned.

[30] Foreign Application Priority Data

Dec. 2, 1978 [DE] Fed. Rep. of Germany ....... 2852275

[51] Int. Cl.³ .................. A01N 43/08; C07D 307/45
[52] U.S. Cl. .................. 424/285; 424/306; 260/465 D; 560/20; 560/57; 560/55; 560/101; 560/104; 560/105; 560/124; 549/499
[58] Field of Search .................. 260/347.2, 347.4; 424/285

[56] References Cited

U.S. PATENT DOCUMENTS 3,857,863 12/1974 Ohno et al. ............... 260/347.4
4,166,064 8/1979 Kondo et al. ............. 260/347.4

OTHER PUBLICATIONS

Matsuo et al., Agr. Biol. Chem. 40 (1), 247-9, (1976).

Primary Examiner—Henry R. Jiles
Assistant Examiner—Bernard Dentz
Attorney, Agent, or Firm—Keil & Witherspoon

[57] ABSTRACT

Novel carboxylic acid esters of the formula

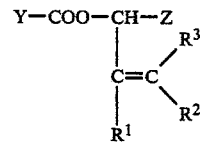

where
$R^1$, $R^2$ and $R^3$ are identical or different and each is hydrogen, halogen or alkyl or alkenyl of up to 5 carbon atoms,
Y is 3-(2,2-dihalogenovinyl)-2,2-dimethyl-cyclopropyl or a radical of the formula

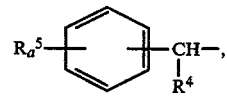

where $R^4$ is unbranched or branched alkyl, alkenyl or alkynyl of up to 4 carbon atoms or is an alicyclic radical of 3 to 7 carbon atoms,
$R^5$ is halogen, alkyl or alkoxy of up to 5 carbon atoms, trihalomethyl, cyano or nitro and
a is from 0 to 3 and
Z is a radical of the formula

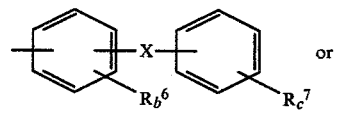 or

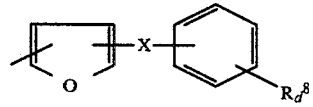

where
X is oxygen, sulfur or —CH$_2$—,
$R^6$, $R^7$ and $R^8$ are halogen or alkyl, alkoxy or haloalkyl of up to 5 carbon atoms and
b, c and d are from 0 to 3, their preparation and their use in insect and arachnid control.

6 Claims, No Drawings

INSECTICIDAL BENZYLFURYLMETHYL ESTERS OF 3-(2,2-DICHLOROVINYL)-2,2-DIMETHYL-CYCLOPROPANE CARBOXYLIC ACIDS

This is a continuation of application Ser. No. 096,520, filed Nov. 21, 1979, now abandoned.

The present invention relates to novel carboxylic acid esters, pest control agents which contain these esters as active ingredients, and a process for pest control using these active ingredients.

The insecticidal activity of 2,2-dimethyl-3-(2',2'-dimethylvinyl)-cyclopropanecarboxylic acid esters, where the alcohol component is a furylmethyl radical substituted by alkenyl in the α-position, is disclosed in Belgian Pat. No. 770,874. Further, Agr. Biol. Chem. 37 (1973), 2,681 discloses that 2,2-dimethyl-3-(2',2'-dimethylvinyl)-cyclopropanecarboxylic acid 3''-phenoxybenzyl ester, substituted by vinyl in the α-position of the phenoxybenzyl radical is insecticidally active. However, the compound is less active insecticidally than the ester which contains the unsubstituted 3-phenoxybenzyl radical as the alcohol component (Agr. Biol. Chem. 40 (1976), 247-249).

We have found that novel carboxylic acid esters of the formula I

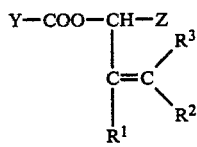

where
- $R^1$, $R^2$ and $R^3$ are identical or different and each is hydrogen, halogen or alkyl or alkenyl of up to 5 carbon atoms,
- Y is 3-(2,2-dihalogenovinyl)-2,2-dimethyl-cyclopropyl or a radical of the formula

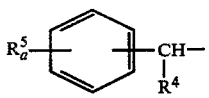

wherein $R^4$ is unbranched or branched alkyl, alkenyl or alkynyl of up to 4 carbon atoms or is an alicyclic radical of 3 to 7 carbon atoms,
$R^5$ is halogen, alkyl or alkoxy of up to 5 carbon atoms, trihalomethyl, cyano or nitro and
a is from 0 to 3 and
Z is a radical of the formula

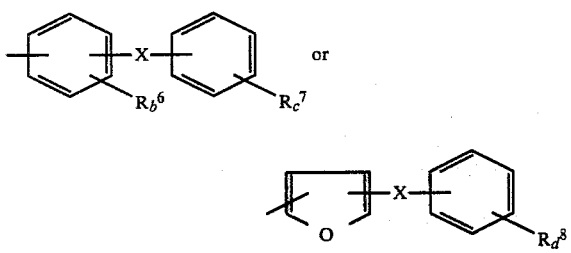

where

X is oxygen, sulfur or —CH$_2$—,
$R^6$, $R^7$ and $R^8$ are halogen or alkyl, alkoxy or haloalkyl of up to 5 carbon atoms and
b, c and d are from 0 to 3, are very suitable for pest control, especially for the control of insects and arachnidae.

In formula I, Y is a 3-(2,2-dihalovinyl)-2,2-dimethyl-propyl radical, for example 3-(2,2-dichlorovinyl)-2,2-dimethyl-cyclopropyl, 3-(2,2-dibromovinyl)-2,2-dimethylcyclopropyl or 3-(2,2-difluorovinyl)-2,2-dimethylcyclopropyl or a radical of the formula

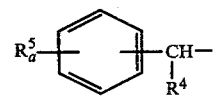

which may have up to three identical or different substituents $R^5$ in the phenyl ring. Suitable substituents $R^5$ are halogen, eg. fluorine, chlorine or bromine, trihalomethyl, eg. trifluoromethyl or trichloromethyl, cyano, nitro or unbranched or branched alkyl or alkoxy of up to 5 carbon atoms, eg. methyl, methoxy, ethyl, ethoxy, n-propyl, isopropyl, tert.-butyl, isobutyl, pentyl, isopentyl, n-propoxy, n-butoxy, isopropoxy, sec.-butoxy, isobutoxy, n-pentoxy or isopentoxy.

$R^4$ may be unbranched or branched alkyl, alkenyl or alkynyl of up to 4 carbon atoms, eg. methyl, ethyl, isopropyl, tert.-butyl, isobutyl, allyl, isopropenyl or propargyl, or an alicyclic radical of 3 to 7 carbon atoms, eg. cyclopropyl or cyclohexyl.

Z in the formula I is a radical of the formulae

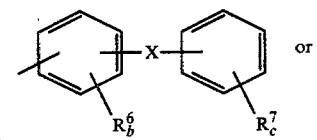 or

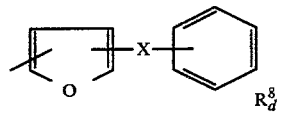

where X is oxygen, sulfur or methylene, for example 3-phenoxyphenyl, 5-benzyl-fur-3-yl, 5-phenoxy-fur-3-yl, 5-phenoxy-fur-2-yl, 3-benzylphenyl, 3-phenylthiophenyl and 5-phenylthio-fur-3yl. The phenyl rings in the formulae of the radicals Z may be unsubstituted or have up to three identical or different substituents. Suitable substituents $R^6$, $R^7$ and $R^8$ are halogen, for example fluorine, chlorine or bromine, or unbranched or branched alkyl, alkoxy or haloalkyl of up to 5 carbon atoms, eg. methyl, ethyl, propyl, isopropyl, n-butyl, tert.-butyl, isobutyl, isomeric pentyl radicals, methoxy, ethoxy, n-propoxy, isopropoxy, isomeric butoxy or pentoxy radicals, trifluoromethyl or trichloromethyl.

$R^1$, $R^2$ and $R^3$ in formula I are, independently of one another, hydrogen, halogen, eg. fluorine, chlorine or bromine, or unbranched or branched alkyl or alkenyl of up to 5 carbon atoms, eg. methyl, ethyl, n-propyl, isopropyl, butyl, tert.-butyl, n-pentyl, isopentyl, vinyl, allyl, n-propenyl, isopropenyl, n-butenyl, n-pentenyl, 1-methyl-n-propenyl or 1-methyl-n-butenyl.

Preferred compounds of the formula I are those where Y is 3-(2,2-dihalovinyl)-2,2-dimethyl-cyclopropyl or α-isopropylbenzyl monosubstituted in the phenyl ring by fluorine, chlorine, bromine or alkoxy of up to 5 carbon atoms, Z is 3-phenoxy-phenyl or 5-benzyl-fur-3-yl and $R^1$, $R^2$ and $R^3$ are hydrogen or fluorine.

Examples of esters according to the invention, of the formula I, are 2,2-dimethyl-3-(2',2'-dichlorovinyl)-cyclopropanecarboxylic acid 3-phenoxy-α-vinylbenzyl ester, 2,2-dimethyl-3-(2',2'-dibromovinyl)-cyclopropylcarboxylic acid 3-phenoxy-α-vinyl-benzyl ester, 2,2-dimethyl-3-(2',2'-difluorovinyl)-cyclopropanecarboxylic acid 3-phenoxy-α-vinyl-benzyl ester, 2-(4-chlorophenyl)-isovaleric acid 3-phenoxy-α-vinyl-benzyl ester, 2,2-dimethyl-3-(2',2'-difluorovinyl)-cyclopropanecarboxylic acid 5-benzyl-α-vinyl-furfur-3-yl ester, 2,2-dimethyl-3-(2',2'-difluorovinyl)-cyclopropanecarboxylic acid 5-benzyl-α-(2-methyl-prop-1-enyl)-furfur-3-yl ester, 2,2-dimethyl-3-(2',2'-difluorovinyl)-cyclopropanecarboxylic acid 3-phenoxy-α-(2-methyl-prop-1-enyl)-benzyl ester, 2,2-dimethyl-3-(2',2'-difluorovinyl)-cyclopropanecarboxylic acid 5-benzyl-α-isopropenyl-furfur-3-yl ester, 2,2-dimethyl-3-(2',2'-difluorovinyl)-cyclopropanecarboxylic acid 5-benzyl-α-(n-but-1-enyl)-furfur-3-yl ester, 2,2-dimethyl-3-(2',2'-difluorovinyl)-cyclopropanecarboxylic acid 3-phenoxy-α-(n-prop-1-enyl)-benzyl ester, 2,2-dimethyl-3-(2',2'-difluorovinyl)-cyclopropanecarboxylic acid 3-(4-chlorophenoxy)-α-(1-chloroprop-1-enyl)-benzyl ester, 2,2-dimethyl-3-(2',2'-difluorovinyl)-cyclopropanecarboxylic acid 3-phenoxy-α-(n-but-1-enyl)-benzyl ester, 2,2-dimethyl-3-(2',2'-difluorovinyl)-cyclopropanecarboxylic acid 5-benzyl-α-(2,2-dichlorovinyl)-furfur-3-yl ester, 2,2-dimethyl-3-(2',2'-dibromovinyl)-cyclopropanecarboxylic acid 3-phenoxy-α-isopropenyl-benzyl ester, 2,2-dimethyl-3-(2',2'-dibromovinyl)cyclopropanecarboxylic acid 3-phenoxy-α-(2,2-dichlorovinyl)-benzyl ester, 2,2-dimethyl-3-(2',2'-dibromovinyl)-cyclopropanecarboxylic acid 5-benzyl-α-(n-prop-1-enyl)-furfur-3-yl ester, 2,2-dimethyl-3-(2',2'-dibromovinyl)-cyclopropanecarboxylic acid 5-(4-fluorophenyl)-α-vinyl-furfur-3-yl ester, 2,2-dimethyl-3-(2',2'-dibromovinyl)-cyclopropanecarboxylic acid 3-benzyl-α-vinyl-benzyl ester, 2-(4-chlorophenyl)-isovaleric acid 3-phenylthio-α-vinyl-benzyl ester, 2-(4-chlorophenyl)-isovaleric acid 3-phenoxy-α-(1-chlorovinyl)-4-fluoro-benzyl ester, 2-(4-chlorophenyl)-isovaleric acid 3-(4-fluorophenyl)-α-vinyl-benzyl ester, 2-(4-chlorophenyl)-isovaleric acid 3-phenoxy-α-trifluoro-vinyl benzyl ester, 2,2-dimethyl-3-(2',2'-dichlorovinyl)-cyclopropanecarboxylic acid 3-phenoxy-α-isopropenyl-benzyl ester, 2,2-dimethyl-3-(2',2'-dichlorovinyl)-cyclopropanecarboxylic acid 3-phenoxy-α-(2,2-dichlorovinyl)-benzyl ester, 2,2-dimethyl-3-(2',2'-dichlorovinyl)-cyclopropanecarboxylic acid 5-benzyl-α-(n-prop-1-enyl)-furfur-3-yl ester, 2,2-dimethyl-3-(2',2'-dichlorovinyl)-cyclopropanecarboxylic acid 5-(4-fluorophenyl)-α-vinyl-furfur-3-yl ester, 2,2-dimethyl-3-(2',2'-dichlorovinyl)-cyclopropanecarboxylic acid 3-benzyl-α-vinyl-benzyl ester, 2,2-dimethyl-3-(2',2'-dichlorovinyl)-cyclopropanecarboxylic acid 3-phenyl-thio-α-vinyl-benzyl ester, 2,2-dimethyl-3-(2',2'-dichlorovinyl)-cyclopropanecarboxylic acid 3-phenoxy-α-(1-chlorovinyl)-4-fluoro-benzyl ester, 2,2-dimethyl-3-(2',2'-dichlorovinyl)-cyclopropanecarboxylic acid 3-(4-fluorophenoxy)-α-vinyl-benzyl ester, 2,2-dimethyl-3-(2',2'-dichlorovinyl)-cyclopropanecarboxylic acid 3-phenoxy-α-trifluorovinyl-benzyl ester, 2,2-dimethyl-3-(2',2'-dichlorovinyl)-cyclopropanecarboxylic acid 3-(4-chlorophenoxy)-α-(1-chloro-n-prop-1-enyl)-benzyl ester, 2-(4-chlorophenyl)-isovaleric acid 3-phenoxy-α-(n-prop-1-enyl)-benzyl ester, 2-(4-chlorophenyl)-isovaleric acid 3-(4-chlorophenoxy)-α-(1-chloroprop-1-enyl)-benzyl ester, 2-(4-chlorophenyl)-isovaleric acid 3-phenoxy-α-(n-but-1-enyl)-benzyl ester, 2-(4-chlorophenyl)-isovaleric acid 5-benzyl-α-(2,2-dichlorovinyl)-furfur-3-yl ester, 2,2-dimethyl-(2',2'-dibromovinyl)-cyclopropanecarboxylic acid 5-benzyl-α-vinyl-furfur-3-yl ester, 2,2-dimethyl-(2',2'-dibromovinyl)-cyclopropanecarboxylic acid 5-benzyl-α-(2-methyl-prop-1-enyl)-furfur-3-yl ester, 2,2-dimethyl-(2',2'-dibromovinyl)-cyclopropanecarboxylic acid 3-phenoxy-α-(2-methyl-prop-1-enyl)-benzyl ester, 2,2-dimethyl-(2',2'-dibromovinyl)-cyclopropanecarboxylic acid 5-benzyl-α-isopropenyl-furfur-3-yl ester, 2,2-dimethyl-(2',2'-dibromovinyl)-cyclopropanecarboxylic acid 5-benzyl-α-(n-but-1-enyl)-furfur-3-yl ester, 2,2-dimethyl-(2',2'-dibromovinyl)-cyclopropanecarboxylic acid 3-phenoxy-α-(n-prop-1-enyl)-benzyl ester, 2,2-dimethyl-(2',2'-dibromovinyl)-cyclopropanecarboxylic acid 3-phenoxy-α-(n-but-1-enyl)-benzyl ester, 2,2-dimethyl-(2',2'-dibromovinyl)-cyclopropanecarboxylic acid 5-benzyl-α-(2,2-dichlorovinyl)-furfur-3-yl ester, 2,2-dimethyl-3-(2',2'-difluorovinyl)-cyclopropanecarboxylic acid 3-phenoxy-α-isopropenyl-benzyl ester, 2,2-dimethyl-3-(2',2'-difluorovinyl)-cyclopropanecarboxylic acid 3-phenoxy-α-(2,2-dichlorovinyl)-benzyl ester, 2,2-dimethyl-3-(2',2'-difluorovinyl)-cyclopropanecarboxylic acid 5-benzyl-α-(n-prop-1-enyl)-furfur-3-yl ester, 2,2-dimethyl-3-(2',2'-difluorovinyl)-cyclopropanecarboxylic acid 5-(4-fluorophenyl)-α-vinyl-furfur-3-yl ester, 2,2-dimethyl-3-(2',2'-difluorovinyl)-cyclopropanecarboxylic acid 3-benzyl-α-vinyl-benzyl ester, 2,2-dimethyl-3-(2',2'-difluorovinyl)-cyclopropanecarboxylic acid 3-phenylthio-α-vinyl-benzyl ester, 2,2-dimethyl-3-(2',2'-difluorovinyl)-cyclopropanecarboxylic acid 3-phenoxy-α-(1-chlorovinyl)-4-fluoro-benzyl ester, 2,2-dimethyl-3-(2',2'-difluorovinyl)-cyclopropanecarboxylic acid 3-(4-fluorophenoxy)-α-vinyl-benzyl ester, 2,2-dimethyl-3-(2',2'-difluorovinyl)-cyclopropanecarboxylic acid 3-phenoxy-α-trifluorovinyl-benzyl ester, 2,2-dimethyl-3-(2',2'-dibromovinyl)-cyclopropanecarboxylic acid 3-phenylthio-α-vinyl-benzyl ester, 2,2-dimethyl-3-(2',2'-dibromovinyl)-cyclopropanecarboxylic acid 3-phenoxy-α-(1-chlorovinyl)-4-fluoro-benzyl ester, 2,2-dimethyl-3-(2',2'-dibromovinyl)-cyclopropanecarboxylic acid 3-(4-fluorophenoxy)-α-vinyl-benzyl ester, 2,2-dimethyl-3-(2',2'-dibromovinyl)-cyclopropanecarboxylic acid 3-phenoxy-α-trifluorovinyl-benzyl ester, 2,2-dimethyl-3-(2',2'-dibromovinyl)-cyclopropanecarboxylic acid 3-(4-chlorophenoxy)-α-(1-chloro-n-prop-1-enyl)-benzyl ester, 2-(4-chlorophenyl)-isovaleric acid 5-benzyl-α-vinyl-furfur-3-yl ester, 2-(4-chlorophenyl)-isovaleric acid 5-benzyl-α-(2-methyl-prop-1-enyl)-furfur-3-yl ester, 2-(4-chlorophenyl)-isovaleric acid 3-phenoxy-α-(2-methyl-prop-1-enyl)-benzyl ester, 2-(4-chlorophenyl)-isovaleric acid 5-benzyl-α-isopropenyl-furfur-3-yl ester, 2-(4-chlorophenyl)-isovaleric acid 5-benzyl-α-(n-but-1-enyl)-furfur-3-yl ester, 2,2-dimethyl-3-(2',2'-dichlorovinyl)-cyclopropanecarboxylic acid 5-benzyl-α-vinyl-furfur-3-yl ester, 2,2-dimethyl-3-(2',2'-dichlorovinyl)-cyclopropanecarboxylic acid 5-benzyl-α-(2-methyl-prop-1-enyl)-furfur-3-yl ester, 2,2-dimethyl-3-(2',2'-dichlorovinyl)-cyclopropanecarboxylic acid 3-phenoxy-α-(2-methyl-prop-1-enyl)-benzyl ester, 2,2-dimethyl-3-(2',2'-dichlorovinyl)-cyclopropanecarboxylic acid 5-benzyl-α-isopropenylfurfur-3-yl ester, 2,2-dimethyl-3-(2',2'-dichlorovinyl)-cyclopropanecarboxylic acid 5-benzyl-α-(n-but-1-enyl)-furfur-3-yl ester, 2,2-dimethyl-3-(2',2'-dichlorovinyl)-cyclopropanecarboxylic acid 3-phenoxy-α-(n-prop-1-enyl)-benzyl ester, 2,2-dimethyl-3-(2',2'-dichlorovinyl)-cyclopropanecarboxylic acid 3-phenoxy-α-(n-but-1-enyl)-benzyl ester, 2,2-dimethyl-3-(2',2'-dichlorovinyl)-cyclopropanecarboxylic acid 5-benzyl-α-(2,2-dichlorovinyl)-furfur-3-yl ester, 2-(4-chlorophenyl)-isovaleric acid 3-phenoxy-α-isopropenyl-benzyl ester, 2-(4-chlorophenyl)-isovaleric acid 3-phenoxy-α-(2,2-dichlorovinyl)benzyl ester, 2-(4-chlorophenyl)-isovaleric acid 5-benzyl-α-(n-prop-1-enyl)-furfur-3-yl ester, 2-(4-chlorophenyl)-isovaleric acid 5-(4-fluorophenyl)-α-vinyl-furfur-3-yl ester and 2-(4-chlorophenyl)-isovaleric acid 3-benzyl-α-vinyl-benzyl ester. Of course, the name of the ester in each case embraces all possible isomers.

The novel carboxylic acid esters of the formula I may be obtained by reacting an acid halide of the formula II Y-CO-Hal      II where Y has the above meanings and Hal is halogen, especially chlorine, with a compound of the formula III

III where $R^1$, $R^2$, $R^3$ and Z have the above meanings, in the presence of an acid acceptor. Furthermore, the novel esters of the formula I may be prepared by reacting an acid of the formula IV

Y-COOH      IV where Y has the above meanings, with a halide of the formula V

V where $R^1$, $R^2$, $R^3$ and Z have the above meanings and Hal is halogen, especially chlorine, in the presence of an acid acceptor.

Further methods of synthesis are the reaction of an acid of the formula IV with a compound of the formula III in the presence of a water-binding agent, and the reaction of an alkyl ester of the formula VI

Y-COOR      VI where Y has the above meanings and R is unbranched or branched alkyl of 1 to 5 carbon atoms, with a compound of the formula III in the presence of a conventional trans-esterifying catalyst.

The individual methods can be represented by the following equations:

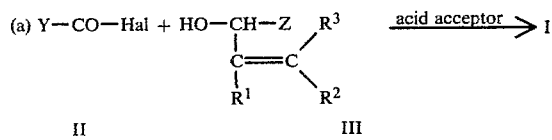

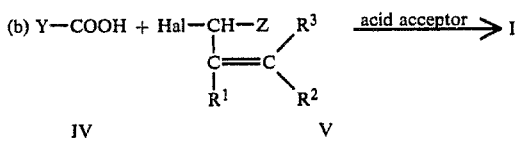

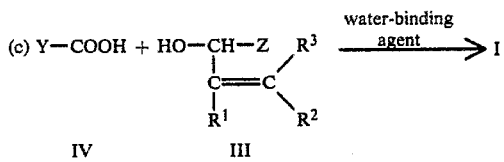

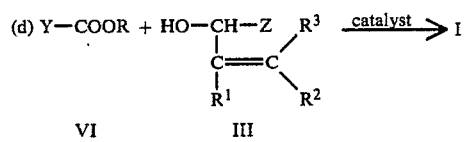

Suitable acid acceptors for synthesis methods (a) and (b) are organic bases, for example tertiary amines, eg. triethylamine, trimethylamine, dimethylaniline, dimethylbenzylamine or pyridine, and inorganic bases, such as hydroxides, oxides, bicarbonates or carbonates of alkali metals or alkaline earth metals, eg. sodium hydroxide, potassium hydroxide, calcium hydroxide, calcium bicarbonate or potassium carbonate, and alcoholates or hydrides of the alkali metals, eg. sodium hydride or potassium t.-butylate. The acid acceptor is employed in at least the molar amount, based on the compound of the formula II or V.

Examples of suitable water-binding agents for the reaction according to equation (c) are dicyclohexylcarbodiimide, inorganic mineral acids, eg. sulfuric acid or phosphoric acid, acid ion exchangers or p-toluenesulfonic acid. The water-binding agent is used in an amount of at least 0.02, advantageously from 0.05 to 0.4 mole, based on the reactant III or IV, whichever is present in less than stoichiometric amount.

Suitable catalysts for the trans-esterification according to equation (d) are hydrides or alcoholates of the alkali metals, eg. sodium hydride, sodium ethylate and triphenyl-sodium. Alcoholates of the elements of group IV b of the periodic table, eg. titanium tetramethylate and titanium tetraethylate, may also be used. Advantageously, from 0.02 to 0.4 mole of catalyst is added per mole of ester of the formula VI.

All the methods of preparation (a) to (d) are carried out at reaction temperatures of from −10° to +150° C., under atmospheric or superatmospheric pressure.

To carry out the process, the reactants of the formulae II and III, IV and V, IV and III or VI and III are preferably employed in the equimolar ratio. An excess of one or other component offers no substantial advantages. The reaction takes place virtually quantitatively.

Processes (a) to (d) are advantageously carried out in the presence of a suitable solvent or diluent. Virtually all inert organic solvents may be used for this purpose. They include acyclic and cyclic ethers, eg. diethyl ether, tetrahydrofuran and dioxane, alkylated aliphatic and alicyclic carboxylic acid amides, eg. dimethylformamide and N-methylpyrrolidone, aliphatic and aromatic hydrocarbons and chlorohydrocarbons, eg. toluene, xylenes, chloroform, n-hexane, cyclohexane and chlorobenzene, ketones, eg. acetone and methyl ethyl ketone, nitriles, eg. acetonitrile, dimethylsulfoxide and hexamethylphosphorotriamide. Mixtures of these solvents may also be used.

The process according to equation (a) can also be carried out in aqueous solution. Processes (a) and (b) may also be carried out as two-phase reactions, in which the water-insoluble organic phase used may be, for example, an ether, an aliphatic or aromatic hydrocarbon or chlorohydrocarbon, especially toluene or chloroform, or a ketone, eg. methyl ethyl ketone.

If the starting materials used in the preparation of the esters of the formula I are mixtures of optical isomers or of cis- or trans-isomers, the end products are obtained as mixtures of different optical isomers or cis/trans isomers. These isomer mixtures can be separated into the individual isomers by conventional methods. The term ester of the formula I embraces both the pure isomers and their mixtures.

The starting compounds of the formula II are known from British Pat. No. 1,446,304 and U.S. Pat. No. 3,981,903. The compounds of the formula III may be prepared by conventional methods, for example by reacting an aldehyde with a metal-organyl or by forming an adduct of an alkyne with an aldehyde, followed by partial hydrogenation (Houben-Weyl, Methoden der organischen Chemie, volume V/lb, page 775–790, Georg Thieme Verlag, Stuttgart, 1972). Compounds of the formulae IV, V and VI are also known and can be prepared by conventional methods (U.S. Pat. Nos. 3,979,519 and 3,981,903, Belgian Pat. No. 801,946, and German Laid-Open Applications DOS No. 2,365,555 and DOS No. 2,231,312).

The Examples which follow illustrate the preparation of the esters according to the invention, of the formula I.

EXAMPLE 1

(a) 3-Phenoxy-α-vinyl-benzyl alcohol 30 ml of a 1.6 molar solution of vinyl-magnesium chloride in tetrahydrofuran are introduced into 100 ml of absolute tetrahydrofuran at 0° C. 9.8 g (0.05 mole) of 3-phenoxybenzaldehyde in 100 ml of absolute tetrahydrofuran are added dropwise whilst stirring and excluding moisture. The reaction mixture is stirred for 3 hours at 25° C. and is then cautiously decomposed by adding a cold saturated ammonium chloride solution and a few milliliters of 10% strength hydrochloric acid until the precipitate dissolves. The mixture is then extracted three times by shaking with ether and the combined ether extracts are washed with sodium bisulfite solution, sodium bicarbonate solution and water, dried over sodium sulfate and concentrated under reduced pressure.

9.4 g of a yellowish oil are obtained; this product is sufficiently pure for further reaction.
Calculated: C 79.62 H 6.24 O 14.14 Found: C 79.3 H 6.1 O 14.5

(b) 2,2-Dimethyl-3-(2',2'-dibromovinyl)-cyclopropanecarboxylic acid 3-phenoxy-α-vinyl-benzyl ester 15.8 g (0.05 mole) of 2,2-dimethyl-3-(2',2'-dibromovinyl)-cyclopropanecarboxylic acid chloride are added dropwise, whilst stirring, to 5.1 g (0.05 mole) of pyridine, 100 ml of absolute ether and 11.4 g (0.05 mole) of 3-phenoxy-α-vinyl-benzyl alcohol at 0°–5° C.

After having been stirred for 12 hours at room temperature, the reaction mixture is filtered and the filtrate is successively washed with 2 N sodium bicarbonate solution, 2 N hydrochloric acid and water. After drying over sodium sulfate, the filtrate is concentrated under reduced pressure and the oil obtained is purified by column chromatography over silica gel, using toluene as the eluant.

An isomer mixture of the formula

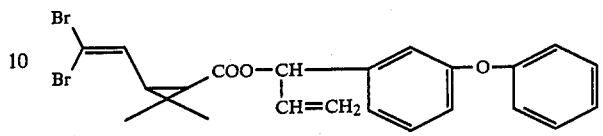

is obtained as a yellowish oil having a refractive index $n_D^{28} = 1.5823$; yield: 8 g.

EXAMPLE 2

(a) 3-Phenoxy-(α-trifluorovinyl)-benzyl alcohol 19.32 g (0.12 mole) of 1-bromo-1,2,2-trifluoroethene are introduced, as a gas, into 100 ml of absolute ether at −78° C. 66.6 ml of a 1.5 N butyl-lithium solution in n-hexane are added dropwise at the same temperature, whilst passing nitrogen through the apparatus. After 30 minutes, a solution of 19.8 g (0.1 mole) of m-phenoxybenzaldehyde in 100 ml of absolute ether is added dropwise to the reaction mixture. When the mixture has returned to room temperature, it is hydrolyzed with a saturated ammonium chloride solution and dilute hydrochloric acid. The ether phase is separated off, washed with a 2 N sodium bicarbonate solution and with water, dried and concentrated. 26 g of a dark red oil, which is sufficiently pure for the subsequent reactions, are obtained.

A small amount of the oil is purified over a silica gel column, using an 85/15 mixture of cyclohexane/acetone. A reddish oil having a refractive index $n_D^{23} = 1.5442$ is isolated.

(b) 2,2-Dimethyl-3-(2',2'-dichlorovinyl)-cyclopropanecarboxylic acid 3-phenoxy-(α-trifluorovinyl)-benzyl ester 14 g (0.05 mole) of 3-phenoxy-(α-trifluorovinyl)benzyl alcohol in 150 ml of absolute ether and 5.6 g (0.06 mole) of γ-picoline are introduced into the apparatus at 0°–5° C. A solution of 11.5 g (0.05 mole) of 2,2-dimethyl-3-(2',2'-dichlorovinyl)-cyclopropanecarboxylic acid chloride in 20 ml of absolute ether is slowly added dropwise. The mixture is stirred overnight at room temperature and is then filtered, and the ether solution is washed with 2 N hydrochloric acid, 2 N sodium bicarbonate solution and water, dried over sodium sulfate and concentrated under reduced pressure. The resulting oil is purified over a silica gel column, using an 85/15 mixture of cyclohexane/acetone as the eluant; yield 10.2 g; $n_D^{25} = 1.5390$.

EXAMPLE 3

(a) 2-Benzyl-(α-vinyl)-benzyl alcohol 30 ml of a 1.6 molar solution of vinyl-magnesium chloride in tetrahydrofuran are introduced into 100 ml of absolute tetrahydrofuran at 0° C. 9.8 g (0.05 mole) of 2-benzylbenzaldehyde in 100 ml of absolute tetrahydrofuran are added dropwise whilst stirring and excluding moisture. The reaction mixture is stirred for 3 hours at 25° C. and is then cautiously decomposed by adding a cold saturated ammonium chloride solution and a few milliliters of 10% strength hydrochloric acid until the precipitate dissolves. The mixture is then extracted by shaking three times with ether and the combined ether phases are washed with sodium bisulfite solution, sodium bicarbonate solution and water, dried over sodium sulfate and concentrated under reduced pressure. 9.4 g of a yellowish oil, which is sufficiently pure for the further reactions, are obtained; $n_D^{21}=1.5855$.

(b)

2,2-Dimethyl-3-(2',2'-dichlorovinyl)-cyclopropanecarboxylic acid 2benzyl-(α-vinyl)-benzyl ester 91 g (0.04 mole) of 2,2-dimethyl-3-(2',2'-dichlorovinyl)-cyclopropanecarboxylic acid chloride are added dropwise, whilst stirring, to 4.6 g (0.05 mole) of γ-picoline, 100 ml of absolute ether and 8.5 g (0.38 mole) of 2-benzyl-(α-vinyl)-benzyl alcohol at 0°-5° C. After having been stirred for 12 hours at 25° C., the reaction mixture is filtered and the filtrate is successively washed with 2 N sodium bicarbonate solution, 2 N hydrochloric acid and water. After drying over sodium sulfate, the filtrate is concentrated under reduced pressure and the resulting oil is purified by column chromatography over silica gel, using toluene as the eluant.

10.3 g of an isomer mixture of the formula

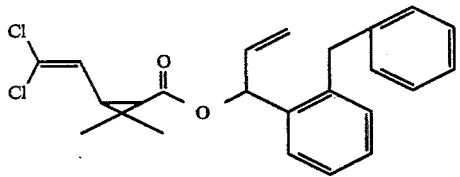

are obtained as a yellowish oil; $n_D^{21}=1.5678$.

EXAMPLE 4

(a) 2-Benzyl-(α-trifluorovinyl)-benzyl alcohol 19.32 g (0.12 mole) of 1-bromo-1,2,2-trifluoroethene are introduced, as a gas, into 100 ml of absolute ether at −78° C. At the same temperature, 66.6 ml of a 1.5 N butyl-lithium solution in n-hexane and 19.6 g (0.1 mole) of 2-benzyl-benzaldehyde in 100 ml of absolute ether are simultaneously added dropwise, in several portions, whilst passing nitrogen through the apparatus. The mixture is allowed to come to room temperature slowly, and is hydrolyzed with a saturated ammonium chloride solution and dilute hydrochloric acid. The ether phase is separated off, washed with 2 N sodium bicarbonate solution and water, dried and concentrated.

The resulting 26.7 g of a dark red oil are sufficiently pure for the further reactions.

A small amount is purified over a silica gel column, using an 85/15 mixture of cyclohexane/acetone. A reddish oil having a refractive index $n_D^{23}=1.5388$ is isolated.

(b)

2,2-Dimethyl-3-(2',2'-dibromovinyl)-cyclopropanecarboxylic acid 2-benzyl-(α-trifluorovinyl)-benzyl ester 11.1 g (0.04 mole) of 2-benzyl-(α-trifluorovinyl)-benzyl alcohol in 100 ml of absolute ether and 4.6 g (0.05 mole) of γ-picoline are first introduced into the apparatus at 0°-5° C. A solution of 19.0 g (0.05 mole) of 2,2-dimethyl-3-(2',2'-dibromovinyl)cyclopropanecarboxylic acid chloride in 20 ml of absolute ether is slowly added dropwise. The mixture is stirred overnight at room temperature and is filtered, and the ether solution is washed with 2 N hydrochloric acid, 2 N sodium bicarbonate solution and water, dried over sodium sulfate and concentrated under reduced pressure. The resulting oil is purified over a silica gel column, using an 85/15 cyclohexane/acetone mixture as the eluant.

10.4 g of an oil of the formula

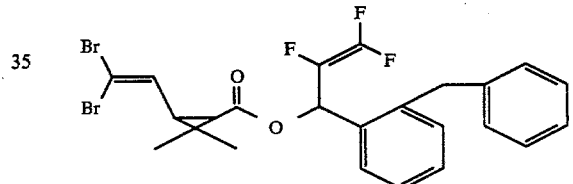

are obtained as an isomer mixture, having a refractive index $n_D^{21}=1.5561$.

The following compounds may be prepared similarly:

$$Y-COO-\underset{\underset{CH=CH_2}{|}}{CH}-Z$$

| No. | Y | Z | $n_D$ |
|---|---|---|---|
| 5 | ![Cl,Cl-vinyl-cyclopropyl] | ![phenoxyphenyl] | $n_D^{23}=1.5628$ |
| 6 | ![Cl,Cl-vinyl-cyclopropyl] | ![furyl-CH2-phenyl] | $n_D^{23}=1.5595$ |
| 7 | ![Br,Br-vinyl-cyclopropyl] | ![furyl-CH2-phenyl] | $n_D^{23}=1.5655$ |
| 8 | ![Cl-phenyl-CH-isopropyl] | ![phenoxyphenyl] | $n_D^{25}=1.5603$ |

-continued
| No. | Y | Z | $n_D$ |
|---|---|---|---|
| 9 | 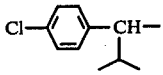 | 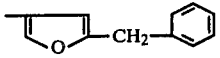 | $n_D^{23} = 1.5630$ |
| 10 | 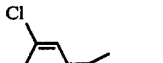 | 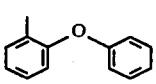 | $n_D^{23} = 1.5621$ |
| 11 | 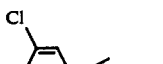 | 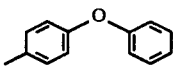 | $n_D^{21} = 1.5672$ |
| 12 | 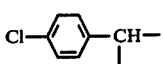 | 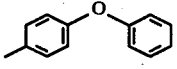 | $n_D^{21} = 1.5721$ |
| 13 |  | 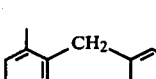 | $n_D^{21} = 1.5810$ |
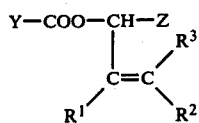
| No. | Y | Z | $R^1$ | $R^2$ | $R^3$ | $n_D$ |
|---|---|---|---|---|---|---|
| 14 | 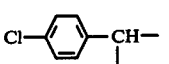 | 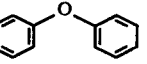 | F | F | F | $n_D^{25} = 1.5422$ |
| 15 |  | 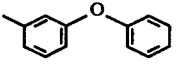 | F | F | F | $n_D^{22} = 1.5515$ |
| 16 |  | 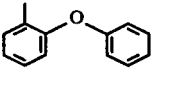 | F | F | F | $n_D^{23} = 1.5358$ |
| 17 | 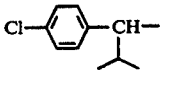 | 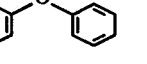 | F | F | F | $n_D^{23} = 1.5351$ |
| 18 | 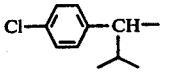 | 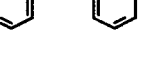 | H | F | F | $n_D^{22} = 1.5553$ |
| 19 | 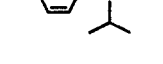 | 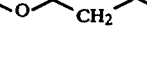 | F | F | F | $n_D^{22} = 1.5320$ |
| 20 |  | 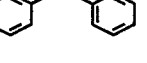 | H | F | F | $n_D^{22} = 1.5626$ |
| 21 |  | 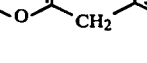 | F | F | F | $n_D^{22} = 1.5452$ |
| 22 |  | 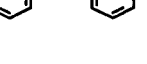 | H | F | F | $n_D^{23} = 1.5572$ |

-continued

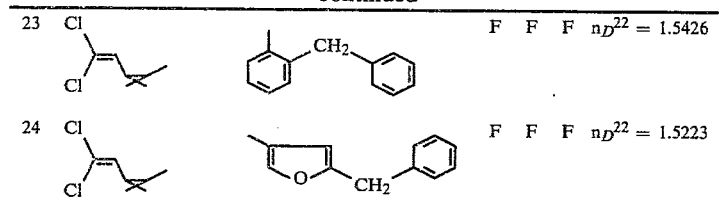

The carboxylic acid esters according to the invention are suitable for effectively combating pests from the class of insects and Arachnida.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami,* and *Musca domestica;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acrythosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the isoptera order are *Reticulitermes lucifugus, Termes natalensis, Calotermes flavicollis* and *Leucotermes flavipes;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femurrubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

The compounds according to the invention may be successfully employed as pesticides for crop protection, and in the hygiene, stores protection and veterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

Examples of formulations are given below:

I. 3 parts of weight of 2,2-dimethyl-3-(2',2'-dibromovinyl)-cyclopropanecarboxylic acid 3-phenoxy-α-vinyl-benzyl ester is intimately mixed with 97 parts by weight of particulate kaolin. A dust is obtained containing 3% by weight of the active ingredient.

II. 30 parts of weight of 3'-phenoxy-α'-vinyl-benzyl-α-isopropyl-4-chlorophenyl acetate is intimately mixed with a mixture consisting of 92 parts by weight of powdered silica gel and 8 parts of weight of paraffin oil which has been sprayed onto the surface of this silica gel. A formulation of the active ingredient is obtained having good adherence.

III. 20 parts by weight of 5'-benzyl-α'-vinyl-furyl-3'-methyl-α-isopropyl-4-chlorophenyl acetate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of 2,2-dimethyl-3-(2',2'-dichlorovinyl)-cyclopropanecarboxylic acid 3-phenoxy-(α-trifluorovinyl)-benzyl-ester is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

There may be added to the individual active ingredients or mixtures thereof (if desired, immediately before use (tankmix)) oils of various types, herbicides, fungicides, insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thioxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O, dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetyl-phosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The compounds of the formula I are particularly advantageously combined with substances which have a synergistic or intensifying effect on pyrethroids. Examples of such compounds are piperonyl butoxide, propynyl ethers, propynyl oximes, propynyl carbamates and propynyl phosphonates, 2-(3,4-methylenedioxyphenoxy)-3,6,9-trioxaundecane, S,S,S-tributylphosphorotrithioate, 1,2-methylenedioxy-4-(2-(octylsulfonyl)-propyl)-benzene, 1-n-dodecylimidazole, 1-(1,5,9-trimethyldecyl)-imidazole, 1-[2-chloro-2-(4-fluorophenyl)-ethyl]-1,2,4-triazole, 1-(2-phenylethyl)-1,2,4-triazole, 1-(2-chloro-2-phenylethyl)-1,2,4-triazole, and 1-(3-phenyl-n-propyl)-1,2,4-triazole. The following examples demonstrate the biological action of the new esters. The agent used for comparison purposes is 2,2-dimethyl-3-(2',2'-dimethylvinyl)-cyclopropanecarboxylic acid-(3-phenoxybenzyl)-ester (Agr. Biol. Chem., 37, 2681, 1973). The numbers of the active ingredients correspond to the manufacturing examples.

EXAMPLE A

Contact action on houseflies (*Musca domestica*)

1 μl of the active ingredient dissolved in acetone is administered by means of a microsyringe to the ventral abdomen of 4-day old imagoes under slight $CO_2$ narcosis. 20 animals treated in the same way are then placed in a plastic bag having a volume of approximately 500 ml.

After 4 hours the animals in supine position are counted and the $LD_{50}$ is determined graphically.

| Active ingredient no. | $LD_{50}$ |
| --- | --- |
| 1 | 0.014 μg/fly |
| 5 | 0.0098 μg/fly |
| comparative agent | 0.017 μg/fly |

EXAMPLE B

Contact action on oriental cockroaches (*Blatta orientalis*)

The bottom of 1-liter preserving jars is treated with acetonic solutions of the active ingredients. After the solvent has evaporated, 5 adult cockroaches are placed in each jar.

The kill rate is determined after 48 hours.

| Active ingredient no. | Amount of active ingredient in mg per preserving jar | Kill rate (%) |
| --- | --- | --- |
| 1 | 0.1 | 100 |
|   | 0.05 | 80 |
| 5 | 0.1 | 100 |
|   | 0.05 | 70 |
| 8 | 0.1 | 100 |
| comparative agent | 0.1 | 20 |

EXAMPLE C

Contact action and effect of ingested food on caterpillars of diamondback moth (*Plutella maculipennis*)

Leaves of young cabbage plants are dipped for 3 seconds in aqueous emulsions of the active ingredients and placed, after excess liquid has been briefly allowed to drip off, on a moist filter paper in a Petri dish. 10 caterpillars of the 4th stage of the diamondback moth are then placed on each leaf.

The action is assessed after 48 hours.

| Active ingredient no. | Kill rate in % at an active ingredient concentration of | |
| --- | --- | --- |
|  | 0.001 wt % | 0.0005 wt % |
| 5 | 100 | 80 |

EXAMPLE D

Contact action on mosquito larvae (Aedes aegypti)

The active ingredient formulations are added to 200 ml of tapwater; 30 to 40 mosquito larvae in the 4th larval stage are then introduced. The temperature is 20° C. The action is determined after 24 hours.

| Active ingredient no. | Concentration of formulation (ppm) | Kill rate (%) |
|---|---|---|
| 5 | 0.01 | 100 |
| 5 | 0.004 | approx. 80 |

EXAMPLE E

Contact action on ticks (Ornithodorus moubata)

Ticks in the 3rd larval stage are placed in paper bags and dipped for 3 seconds in the emulsion under investigation. The bags are then suspended. The action on the ticks is assessed after 48 hours.

| Active ingredient no. | Concentration of active formulation (ppm) | Kill rate (%) |
|---|---|---|
| 5 | 0.0001 | 100 |
| 5 | 0.00005 | 80 |

We claim:

1. A carboxylic acid ester of the formula I

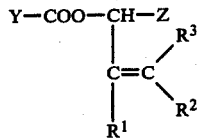

where
R$^1$, R$^2$ and R$^3$ are identical or different and each is hydrogen, halogen or alkyl or alkenyl of up to 5 carbon atoms,
Y is 3-(2,2-dihalogenovinyl)-2,2-dimethyl-cyclopropyl,
Z is a radical of the formula

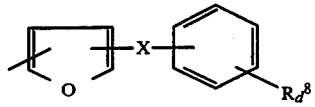

where
X is —CH$_2$—,
R$^8$ is halogen or alkyl, alkoxy or haloalkyl of up to 5 carbon atoms and
d is from 0 to 3.

2. A carboxylic acid ester of the formula I as claimed in claim 1, wherein R$^1$, R$^2$ and R$^3$ denote hydrogen and the substituents Y and Z have the meanings given in claim 1.

3. A carboxylic acid ester of the formula I as claimed in claim 1, wherein R$^1$, R$^2$ and R$^3$ denote fluorine and the substituents Y and Z have the meanings given in claim 1.

4. A carboxylic acid ester of the formula I as claimed in claim 1, wherein Z denotes 5-benzyl-furyl-3 and R$^1$, R$^2$, R$^3$ and Y have the meanings given in claim 1.

5. A insecticide or arachnidicide comprising a solid or liquid carrier and, as active ingredient, an effective amount of a carboxylic acid ester of the formula I

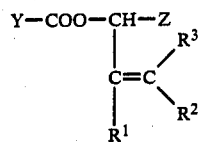

where
R$^1$, R$^2$ and R$^3$ are identical or different and each is hydrogen, halogen or alkyl or alkenyl of up to 5 carbon atoms,
Y is 3-(2,2-dihalogenovinyl)-2,2-dimethyl-cyclopropyl,
Z is a radical of the formula

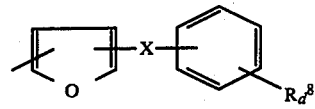

where
X is —CH$_2$—,
R$^8$ is halogen or alkyl, alkoxy or haloalkyl of up to 5 carbon atoms and
d is from 0 to 3.

6. A process for combating insects and arachnids, wherein the insects or arachnids or the objects to be protected against insect and arachnid attack are treated with an effective amount of a carboxylic acid ester of the formula I

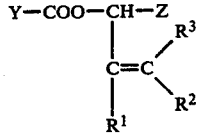

where
R$^1$, R$^2$ and R$^3$ are identical or different and each is hydrogen, halogen or alkyl or alkenyl of up to 5 carbon atoms,
Y is 3-(2,2-dihalogenovinyl)-2,2-dimethyl-cyclopropyl,
Z is a radical of the formula

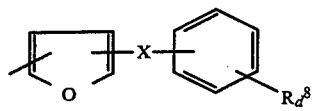

where
X is —CH$_2$—,
R$^8$ is halogen or alkyl, alkoxy or haloalkyl of up to 5 carbon atoms and
d is from 0 to 3.

* * * * *